United States Patent [19]

Termanini

[11] Patent Number: 5,713,838
[45] Date of Patent: Feb. 3, 1998

[54] CURING OF ORTHOPEDIC CASTING MATERIAL AND DEVICE AND METHOD FOR USING SAME

[76] Inventor: Zafer Termanini, 208 Eileen Dr., Cedar Grove, N.J. 07009

[21] Appl. No.: 685,955

[22] Filed: Jul. 22, 1996

[51] Int. Cl.[6] ............................................. A61F 5/00
[52] U.S. Cl. ............................. 602/8; 602/1; 602/79; 602/901
[58] Field of Search ............................. 206/438, 440, 206/441; 602/1, 6–8, 3, 79, 901, 60, 75, 2

[56] References Cited

U.S. PATENT DOCUMENTS

| | | |
|---|---|---|
| 3,521,745 | 7/1970 | Schwartzman ............... 206/47 |
| 3,656,475 | 4/1972 | Hanrahan, Jr. . |
| 3,930,496 | 1/1976 | Gibbons . |
| 3,990,437 | 11/1976 | Boyden, Jr. et al. . |
| 4,019,506 | 4/1977 | Eschmann . |
| 4,060,075 | 11/1977 | Blomer et al. . |
| 4,131,114 | 12/1978 | Kirkpatrick et al. . |
| 4,153,052 | 5/1979 | Tsuk . |
| 4,331,134 | 5/1982 | Brooks et al. . |
| 4,498,467 | 2/1985 | Kirkpatrick et al. . |
| 4,793,330 | 12/1988 | Honeycutt et al. . |
| 5,027,803 | 7/1991 | Scholz et al. ............... 602/8 |
| 5,171,208 | 12/1992 | Edenbaum et al. ............... 602/6 |
| 5,250,344 | 10/1993 | Williamson et al. . |
| 5,476,440 | 12/1995 | Edenbaum . |

FOREIGN PATENT DOCUMENTS

| 2068237 | 8/1991 | United Kingdom ............... 602/6 |
|---|---|---|

*Primary Examiner*—Michael Powell Buiz
*Assistant Examiner*—Chalin Smith
*Attorney, Agent, or Firm*—Ralph T. Lilore, Esq.

[57] ABSTRACT

The disclosure relates to a water-curable orthopedic bandage on a support spool which bandage can be immediately applied to an affected limb. Supplied in addition to the orthopedic bandage and either separately packaged or provided integral with the spool is an amount of a water-laden gel. The word gel is meant to apply to a viscous semi-solid which can be applied over surfaces in an adherent film and will disperse and move in response to the movement of the practitioner's hands in molding and forming the adhesive bandage around the limb. It is to be distinguished from a free-flowing liquid which when applied to a limb drips and causes the messy environment described above.

16 Claims, 1 Drawing Sheet

CURING OF ORTHOPEDIC CASTING MATERIAL AND DEVICE AND METHOD FOR USING SAME

FIELD OF INVENTION

The present invention relates to a novel device comprising an orthopedic bandage wrapped around a piston-like core adapted to expel a water-containing gel and to a method for applying the casting material to an injured limb whereby water contained in a water-laden gel is applied to the casting material to effect its cure.

BACKGROUND OF THE INVENTION

In the orthopedic field it is quite conventional to apply water-curable casting materials to a limb followed by introduction of water into the material to effect curing of the casting material. In the earlier days of the prior art, the cure was effected with plaster of Paris casts by soaking the plaster of Paris laden bandage in water and applying the thus laden bandage to the affected limb. This procedure was both messy and cumbersome, and required additional personnel to assist in application and clean-up.

In more recent times, the technology has advanced to the point where the plaster of Paris has been replaced with certain water-curable resins. The problem of water application, however, to cure the bandage has not been eliminated. It is still necessary to either soak the material in water prior to application and mold and smooth the thus applied casting material or to apply the casting material from a roll and then apply water from buckets or some other available source. This technique still involves the cumbersome, messy technique described above and in addition involves the use of very tacky water-curable resins which prior to being wetted stick to virtually all surfaces including the gloves of the surgeon and adjacent surfaces.

The art has attempted to solve these problems in various ways such as that disclosed in U.S. Pat. No. 5,476,440 which relates to providing a lubricant within the core of the roll supporting the rolled-up bandage prior to application. In use, the surgeon applies the bandage from the roll to the limb and then by squeezing the core which contains holes and perforations for that purpose, squeezes an amount of lubricant onto his hands so that he can rub the lubricant over the tacky curable resin. The use of such a system does not solve the problems referred to above because copious amounts of water are still required to be injected into the core therein to mix with the lubricant and to be applied to the casting material. The disclosure in the aforesaid U.S. Pat. No. 5,476,440 also describes other patents and applications having disclosures intended to solve the above-noted problems. Such disclosure is incorporated herein by reference.

SUMMARY OF THE INVENTION

The present invention finds application to any water-curable casting material including resins normally used in the orthopedic art as well as plaster of Paris casting. The invention also serves the purpose of eliminating the need for any extraneous supply of water other than the components supplied with the rolls of orthopedic bandage either in an integrated form of the orthopedic bandage or supplied separately in a kit with the bandage. More specifically, the invention in its broadest concept relates to a water-curable orthopedic bandage on a support spool which bandage can be immediately applied to an affected limb. Supplied in addition to the orthopedic bandage and either separately packaged or provided integral with the spool is an amount of a water-laden gel. The word gel as used herein is meant to apply to a viscous semi-solid which can be applied over surfaces in an adherent film and will disperse and move in response to the movement of the practitioner's hands in molding and forming the adhesive bandage around the limb. It is to be distinguished from a free-flowing liquid which when applied to a limb drips and causes the messy environment described above.

The invention is suitable for use with any orthopedic casting material that is water-curable. The gel can be any water-laden gel commonly employed in the medical or cosmetics industry or any other that is not so-employed, and is preferably a aqueous phase of the gel system. It may be an emulsified vehicle incorporating water as long as the water becomes available when the gel is rubbed over the applied adhesive bandage. Water emulsions or gels prepared from water and well-recognized gel forming materials such as polymers, thickeners and the like may be used. Materials such as hydroxymethyl, cellulose, acrylates, polygycols and the like are suitable. Materials such as K-Y Jelly and surgical lubricants are preferred.

A suitable kit for carrying out the process of the present invention is a packaged set containing the orthopedic bandage on a support spool and a packaged water-laden gel system provided either separately or as an integral part of the spool as noted above.

When, as is preferable, the gel is supplied in an integrated form with the spool, the spool is preferably adapted to incorporate a piston assemblage wherein the inner walls of the spool act as the container for the gel material with the piston assemblage located so as to provide the means by which the gel may be expelled from the spool. In this embodiment, the spool is also equipped with outlet means which conveniently may have a removable cap thereon to be removed when the piston part of the spool is depressed to expel the gel. In practice, a combination of spool volume and length of piston is selected as will give an appropriate amount of water-laden gel upon expulsion to cure the expected amount of bandage applied to the limb. It is preferred that a volume be chosen such that the length of piston is about equal to the length of the gel-containing segment of the spool to provide for both efficiency and economics of gel utilization.

DETAILED DESCRIPTION OF THE INVENTION

Figure 1:
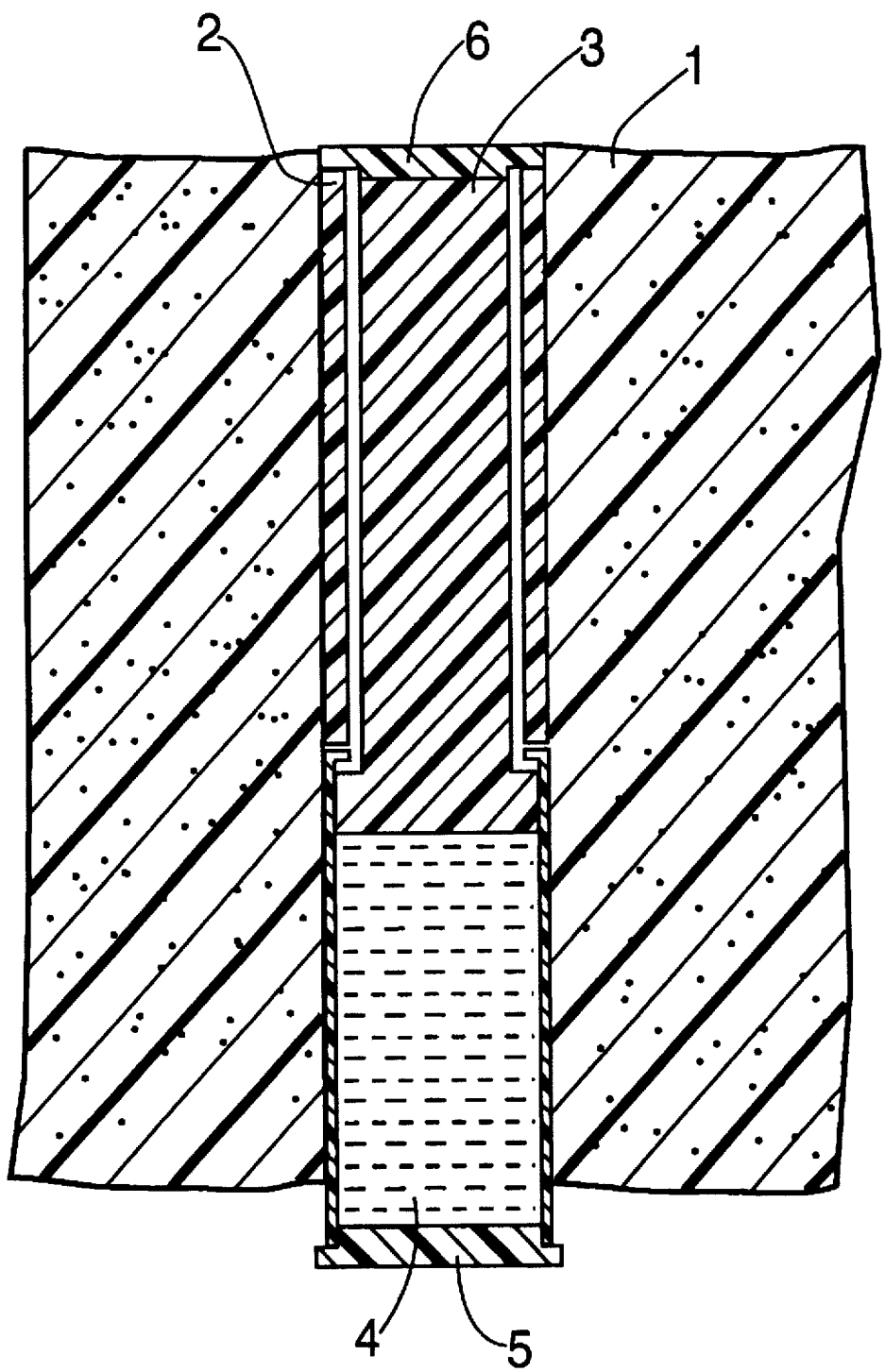

A greater appreciation for an embodiment of the invention will be gained by reference to FIG. 1 wherein a curable casting material 1 is shown rolled around a spool 2. Spool 2 is divided into two segments, piston segment 3 and gel-containing segment 4. Plug cover 5 at the end of gel segment 4 ensures against premature or accidental ejection of the gel material. The piston segment 3 is equipped also with a protective cover 6 to prevent accidental displacement of the piston.

In use, the orthopedic surgeon removes the casting material and applies the same around an appropriately protected limb. At this point, there is no need for the use of any water or other material to be applied to the casting material. Once the casting material has been applied, the surgeon working with one hand, if desired, need only remove covers 5 and 6 by a flick of the finger and depress piston 3 thereby to eject the gel from the gel-holding segment 4 either directly onto portions of the wrapped limb or onto his other gloved hand. He then simply rubs the water-laden gel on, over, and around the applied bandage thereby supplying the water phase to the bandage without any need for extraneously supplied water.

The bandage then cures as it normally would without the normal cumbersome application and water-soaking technique required in the art. The expedient of having the water-laden gel either integrally associated with the support spool or in a separate tube provides a speedy simple application and curing technique that requires no unusual clean-up activities.

As water-curable orthopedic materials there may be mentioned polymers or pre-polymers such as those described in U.S. Pat. No. 5,476,440, but any water-curable materials may be used.

As water-laden gels for use in the present invention virtually any material which can be supplied in a gel-like phase is suitable provided it contains an adequate supply of releasable water. Commercially available materials such products as K-Y Jelly available from SurgiLube, Inc., Long Island, N.Y. and other gel or gelling materials such as polyglycol, hydroxypropyl methylcellulose, propylene glycol, starch, thickeners, and the like may be employed.

The amount of water present in the gel is not critical except to the extent that one wishes to have enough water in the available volume of gel space to provide adequate curing once applied to the bandage system. Gel systems containing too much water, while operative are preferably avoided in order to minimize the amount of free-flowing water and therefore an attendant potential messy situation that requires clean-up. Gels containing too little water are preferably avoided so as to eliminate the need for using large amounts thereof.

There has thus been described a method of curing a water-curable orthopedic bandage casting system and a device and kit for so doing without the need for extraneous amounts of free-flowing water resulting in a simple rapid easily manipulated cast application system.

What is claimed is:

1. An integrated orthopedic bandage system comprising
   a) a spool divided into two segments, a segment containing a water-laden gel and a segment containing a piston assembly wherein said piston assembly is in communication with said gel whereby when said piston is actuated, gel is ejected from said gel-containing segment, and
   b) a water-curable orthopedic casting material unwindingly wrapped around said spool.

2. The system of claim 1 wherein each spool segment is protected by a plug at the ends opposite the point of communication of said gel and said piston assembly.

3. The system of claim 2. wherein the gel comprises a member selected from the group consisting of hydroxymethyl cellulose, hydroxypropyl cellulose, acrylates, polyglycols, and propylene glycol.

4. The system of claim 2 wherein the orthopedic casting material is a resin or plaster-of-paris.

5. An orthopedic bandage kit comprising a package comprising
   a) a water-curable orthopedic casting material unwindingly wrapped around a spool, and
   b) a container comprising a water-laden gel which is removable from said container.

6. The kit of claim 5 where in the gel comprises a member selected from the group consisting of hydroxymethyl cellulose, hydroxypropyl cellulose, acrylates, polyglycols, and propylene glycol.

7. The kit of claim 6 wherein the orthopedic casting material is a resin or plaster-of-paris.

8. The kit of claim 5 wherein the container for said water-laden gel is integrated with said spool.

9. The kit of claim 8 wherein the water-laden gel container is a piston assemblage in communication with said gel whereby when said piston is depressed, gel is ejected from the container.

10. The kit of claim 9 where in the gel comprises a member selected from the group consisting of hydroxymethyl cellulose, hydroxypropyl cellulose, acrylates, polyglycols, and propylene glycol.

11. The kit of claim 10 where in the orthopedic casting material is a resin or plaster-of-paris.

12. A method for curing a water-curable orthopedic casting material which comprises applying to an orthopedic material to be cured, an effective amount of water in the form of a water-laden gel.

13. The method of claim 12 wherein the gel comprises a member selected from the group consisting of hydroxymethyl cellulose, hydroxypropyl cellulose, acrylates, polyglycols, and propylene glycol.

14. The method of claim 12 wherein the orthopedic casting material is a resin or plaster-of-paris.

15. The method of claim 12 wherein the orthopedic casting material is applied from a spool divided into two segments, a segment containing said water-laden gel and a segment containing a piston assembly wherein said piston assembly is in communication with said gel whereby when said piston is actuated, gel is ejected from said gel-containing segment.

16. The method of claim 15 wherein each spool segment is protected by a plug at the ends opposite the point of communication of said gel and said piston assembly.

* * * * *